(12) United States Patent
Magnant

(10) Patent No.: US 10,519,411 B2
(45) Date of Patent: Dec. 31, 2019

(54) CELL CULTURE CASSETTES AND INCUBATOR

(71) Applicant: SAGE SCIENCE, INC., Beverly, MA (US)

(72) Inventor: Gary Paul Magnant, Topsfield, MA (US)

(73) Assignee: Sage Science, Inc., Beverly, MA (US)

(*) Notice: Subject to any disclaimer, the term of this patent is extended or adjusted under 35 U.S.C. 154(b) by 74 days.

(21) Appl. No.: 15/427,887

(22) Filed: Feb. 8, 2017

(65) Prior Publication Data

US 2017/0145366 A1 May 25, 2017

Related U.S. Application Data

(62) Division of application No. 14/211,711, filed on Mar. 14, 2014, now Pat. No. 9,597,355.

(60) Provisional application No. 61/788,745, filed on Mar. 15, 2013, provisional application No. 61/802,976, filed on Mar. 18, 2013.

(51) Int. Cl.
| | |
|---|---|
| *C12M 3/00* | (2006.01) |
| *C12M 1/00* | (2006.01) |
| *C12M 1/12* | (2006.01) |
| *C12M 1/34* | (2006.01) |
| *A61K 35/12* | (2015.01) |

(52) U.S. Cl.
CPC .......... *C12M 23/42* (2013.01); *A61K 35/12* (2013.01); *C12M 23/34* (2013.01); *C12M 25/00* (2013.01); *C12M 41/12* (2013.01); *C12M 41/26* (2013.01); *C12M 41/32* (2013.01); *C12M 41/34* (2013.01); *C12M 41/36* (2013.01)

(58) Field of Classification Search
None
See application file for complete search history.

(56) References Cited

U.S. PATENT DOCUMENTS

| | | | |
|---|---|---|---|
| 1,881,118 A | 10/1932 | Bratton et al. | |
| 8,383,395 B2 | 2/2013 | Hata et al. | |
| 2002/0110905 A1* | 8/2002 | Barbera-Guillem | C12M 23/24 435/294.1 |
| 2006/0257999 A1 | 11/2006 | Chang et al. | |
| 2007/0161106 A1 | 7/2007 | Jervis et al. | |
| 2009/0061416 A1* | 3/2009 | Fang | G01N 33/54373 435/5 |
| 2011/0024630 A1* | 2/2011 | Sundaram | G01N 21/552 250/339.08 |
| 2011/0207209 A1 | 8/2011 | Hammons et al. | |
| 2011/0236932 A1 | 9/2011 | Stobbe | |
| 2011/0263008 A1 | 10/2011 | Wang et al. | |
| 2012/0288939 A1 | 11/2012 | Baker et al. | |

FOREIGN PATENT DOCUMENTS

| | | | | |
|---|---|---|---|---|
| EP | 2130905 A1 | 12/2009 | | |
| WO | WO-2010042072 A1 * | 4/2010 | ........... | C12M 23/44 |

OTHER PUBLICATIONS

Thomas, P.C. et al. 2009. A noninvasive thin film sensor for monitoring oxygen tension during in vitro cell culture. Analytical Chemistry 81: 9239-9246. specif. pp. 9239, 9245, 9246.*
Higuchi, A. et al. 2004. Photon-modulated changes of cell attachments on poly(spiropyran-co-methyl methacrylate) membranes. Biomacromolecules 5: 1770-1774. specif. pp. 1770, 1774.*
S.M. Grist, et al., "Optical Oxygen Sensors for Applications in Microfluidic Cell Culture," Sensors 2010, vol. 10, No. 10 pp. 9286-9316.
International Search Report and Written Opinion of the International Searching Authority, PCT/US2014/027821, 20 pages, dated Aug. 26, 2014.

* cited by examiner

*Primary Examiner* — Renee Claytor
*Assistant Examiner* — Sharon M. Papciak
(74) *Attorney, Agent, or Firm* — Norris McLaughlin, P.A.

(57) ABSTRACT

The invention relates to cassettes for culturing cells. The invention also relates to analytical and preparative incubators for housing the cassettes. The invention also relates to methods of using the cassettes, for example, to culture cells wherein the processes of feeding and passaging cells are automated.

19 Claims, 7 Drawing Sheets

CELL CULTURE CASSETTES AND INCUBATOR

RELATED APPLICATIONS

This present application is a divisional application of application Ser. No. 14/211,711 filed on Mar. 14, 2014 and still pending, which claims priority to U.S. Application No. 61/788,745, entitled "Cell Culture Cassettes and Incubator" and filed Mar. 15, 2013, and U.S. Application No. 61/802,976, entitled "Cell Culture Cassettes and Incubator" and filed Mar. 18, 2013, which are hereby incorporated by reference in their entireties.

TECHNICAL FIELD

The present invention relates to cassettes for cell culture and an analytical and preparative incubator for housing the cassettes.

BACKGROUND OF THE INVENTION

There is a need in the art for efficient and automated methods of culturing cells, especially adherent cells, that allow for culturing large numbers of cells in a single vessel.

BRIEF SUMMARY OF THE INVENTION

The invention relates to a cassette for culturing adherent cells comprising a first film and a second film, wherein the first and/or second film comprises at least one sensor.

In one embodiment, at least one film of the cassette is coated with at least one compound selected from the group consisting of a nutrient, a growth hormone, a cytokine, an antibiotic, an adhesion molecule, a mineral, an antibody, a nucleic acid probe, a primer, an oligonucleotide, an antisense oligonucleotide, a ligand, an enzyme, cell components, cell markers, cells, a dye and a test compound.

In another embodiment, the at least one sensor is present on the first and/or second film.

In another embodiment, the sensor detects at least one of temperature, pH, cell density, $O_2$, $CO_2$, protein, nucleic acid, apoptotic markers, nutrient levels and the rate of consumption of a media component.

In another embodiment, at least a first or second film comprises an adherent layer to which cells can adhere.

In another embodiment, cells adhere to discrete locations on the adherent layer.

In another embodiment, the cassette comprises a frame.

In another embodiment, the at least one sensor is present on the first and/or second film and/or the frame.

In another embodiment, the cassette further comprises an inlet for introducing fluids and an outlet for removing fluids.

In another embodiment, the film comprises a material selected from the group consisting of: polymer films, polyester, polystyrene, surlyn, polyolefins, cyclic olefin polymers, poly(methyl metacrylate), PVDF membranes, cellulose membranes and nylon-semi permeable membranes.

In another embodiment a tissue sample is cultured in the cassette. In another embodiment, the cells are removed from the layer to which they adhere by a method selected from the group consisting of: increasing or decreasing the pH, increasing or decreasing light exposure, and enzymatic degradation.

In another embodiment, the cassette comprises more than one compartment.

In another embodiment, each compartment comprises a sensor.

In another embodiment, the sensor of each compartment is different.

In another embodiment, the film comprising each compartment is coated with at least one compound selected from the group consisting of a nutrient, a growth hormone, a cytokine, an antibiotic, an adhesion molecule, a mineral, an antibody, a nucleic acid probe, a primer, an oligonucleotide, an antisense oligonucleotide, a ligand, an enzyme, cell components, cell markers, cells, a dye and a test compound.

The invention also relates to a method of culturing cells comprising incubating cells in the cassette.

In one embodiment, the method includes a step of feeding the cells, wherein feeding is automated.

In another embodiment, the method includes a step of passaging the cells, wherein passaging is automated.

In another embodiment, at least a first or second film comprises an adherent layer to which cells can adhere.

In another embodiment, cells adhere to discrete locations on the adherent layer.

In another embodiment, the cells are removed from the layer to which they adhere by a method selected from the group consisting of: increasing or decreasing the pH, increasing or decreasing light exposure, and enzymatic degradation.

In another embodiment, at least one film of the cassette is coated with a compound of interest.

In another embodiment, the cassette is housed in an incubator.

The invention also relates to a method of treating a disease in a subject in need thereof comprising; removing cells from the subject; transferring the cells into the cassette, culturing the cells in the presence of at least one agent that is identified as treating the disease; and reintroducing the cells into the subject, thereby treating the disease.

In one embodiment, the method further comprises measuring the level of an activity of the cell known to be associated with a disease and/or measuring the level of expression of a marker known to be associated with a disease; and comparing the level of activity or expression before and after the step of culturing.

In another embodiment, the method further comprises comparing the level or activity of cells of the subject with the level or activity of cells of a control subject that is diagnosed with the disease.

In another embodiment, following the step of culturing there is a modulation in activity or expression, thereby treating the disease.

In another embodiment, modulation comprises a decrease in activity and/or expression.

In another embodiment, modulation comprises an increase in activity and/or expression.

In another embodiment, the agent is present in culture media.

In another embodiment, the first and or second film is coated with the agent.

In another embodiment, the disease is selected from the group recited herein below.

The invention also relates to a method of diagnosing a subject comprising: removing cells from the subject; transferring the cells into a cassette; measuring the level of an activity of the cell known to be associated with a disease and/or measuring the level of expression of a marker known to be associated with a disease.

In one embodiment, the method further comprises a step of comparing the level or activity of cells of the subject with the level or activity of cells of a control subject that is not diagnosed with the disease.

The invention also relates to a method of monitoring the progression of a disease in a subject comprising: removing cells from the subject; transferring the cells to a cassette; measuring the level of an activity of the cell known to be associated with a disease and/or measuring the level of expression of a marker known to be associated with a disease, wherein the level of an activity of a cell or the level of expression of a marker is indicative of the progression of the disease.

In one embodiment, the method further comprises a step of comparing the activity or expression to the activity or expression of cells isolated from the subject at an earlier time point, wherein an increase or a decrease in the level of activity or expression as compared to an earlier time point indicates the progression of the disease.

The invention also relates to a method of designing a treatment protocol for a subject diagnosed with a disease comprising; removing cells from the subject; transferring the cells into a cassette, culturing the cells in the presence of at least one agent that is identified as increasing or decreasing the function of a cell; measuring the level of an activity of the cell known to be associated with a disease and/or measuring the level of expression of a marker known to be associated with a disease, wherein, if the agent increases or decreases the function of the cells of the subject, treating the subject with the agent.

In another embodiment, the agent is present in culture media.

In another embodiment, the agent is present on at least the first or second film.

The invention also relates to a method of screening for a compound for treating a disease comprising: culturing cells isolated from a subject diagnosed with the disease in a cassette in the presence of a test compound; measuring the level of an activity of the cell known to be associated with a disease and/or measuring the level of expression of a marker known to be associated with a disease.

In one embodiment, modulation of activity or expression identifies the compound as treating the disease.

In another embodiment, the method further comprises a step of comparing the level of activity or expression of cells cultured in the presence of the compound with the level of activity or expression of cells cultured in the absence of the compound.

The invention also relates to a method of screening for a compound comprising an activity of interest comprising: culturing cells in a cassette in the presence of a test compound; and; measuring the level of the activity.

In another embodiment, the method further comprises a step of comparing the level of activity or expression of cells cultured in the presence of the compound with the level of activity or expression of cells cultured in the absence of the compound.

The invention also relates to a method of producing a molecule of interest comprising culturing cells engineered to produce the molecule in a cassette, under conditions wherein the molecule is produced.

In one embodiment, the molecule is a protein or an antibody.

In another embodiment, the method further comprises isolating the molecule from the cassette.

In one embodiment, there is provided an incubator. The incubator includes a housing and a computing device disposed within the housing. The incubator also includes a chassis that is coupled to the housing and configured to receive a plurality of cassettes for culturing cells. The chassis includes a plurality of ports that are coupled to the computing device and configured to interface with corresponding connectors of the cassettes that receive data from sensors disposed within the cassettes. The incubator includes a fluidic manifold that houses a media. A conduit of the fluidic manifold includes a plurality of nodes configured to interface with corresponding nodes on cassettes. The computing device is configured to receive a schedule of processes to apply to cell cultures in cassettes; receive and store data regarding environmental conditions within the cassettes; and operate the incubator according to the schedule of processes and received data regarding the environmental conditions.

In some embodiments, the computing device is configured to operate the incubator according to received data regarding the temperature, gas levels, pH level, reagent concentrations, or cell density within a cassette. The computing device may be configured to operate the fluidic manifold to passage a cell culture in a cassette. The computing device may be configured to operate the fluidic manifold to flow a media into a cell culture in a cassette. The computing device may be configured to operate the fluidic manifold to extract contents of a cassette.

In some embodiments, the computing device is configured to store the received data on a remote server. In many embodiments, the computing device is configured to send an alert to a user when a condition of a process is met. The computing device may be configured to wait for a response from a user before executing a process on a cell culture in a cassette.

In many embodiments, the incubator includes an image capturing device coupled to the computing device. The computing device is configured to operate the robotic arm to position the image capturing device over a cassette. In some embodiments, the incubator includes a display for displaying the received data regarding the environmental conditions within the cassettes.

In another embodiment, a method of operating an incubator includes storing, by a computing device, parameters for a schedule of processes to apply to cell cultures in cassettes. The method also monitors data regarding environmental conditions within the cassettes. The method includes matching received data about the environment conditions with at least one parameter for a process on the schedule. The method includes applying the process to the cell culture within the cassettes.

In some embodiment, the method includes receiving the parameters from a user interface of the incubator. In other embodiments, the method includes receiving the parameters from a remote server. The method may include monitoring data received through a port coupled to a chassis of the incubator. The method may include passaging the cell culture in a cassette. The method may include flowing a media into a cassette. The method may include extracting the cell culture from a cassette.

In some embodiments, the system will include liquid handling robotics, especially microtiter (SBS) format systems, which enable the addition and removal of samples or reagents to and from the cassettes, thereby enabling reagents such as drugs, dyes, or fluorescent probes to be added to the cells, or enabling sampled cells or media to be removed from the cassette.

In some embodiments, the system will have the ability to perform analytical functions, including microscopy, mass spectrometry, and nucleic acid sequencing.

In some embodiments, the system will have the capability to genotype or sequence cells to confirm the identity of cell lines without the need for human intervention. This technology can further identify the presence of and nature of contaminants.

In some embodiments, the system will be used to propagate primary culture isolates, including cancer and stem cells, or will be used to grow sheets or masses of organ tissues, such as layers of epithelial and other cells needed for skin grafts.

In some embodiments, the system will be able to function in a diagnostic capacity, especially for the detection of diseases.

In some embodiments the microfluidic systems will be disposable to maintain sterility, and in other embodiments the system and its components will be sterilizable by internal or external sterilization methods. These include the application of chemicals such as bleach, or heat, or pressure, or sterilizing gases, or plasma treatment, or combinations thereof.

In some embodiments the system may include cassettes with film battery or capacitors that enable the cassette itself to perform work, such as monitoring sensors, injecting reagents, or extracting samples.

In some embodiments, the multi-layered coated film on each cassette will have layers that confer a function, such as enabling or optimizing cell adhesion, serving as optical filters, or serving to minimize or maximize the transfer of fluids to each cassette.

In some embodiments that cassettes will be connected in bricks of 10 or more cassettes, enabling large numbers of cassettes to be easily installed or removed from the system.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF THE INVENTION

Figure 1:
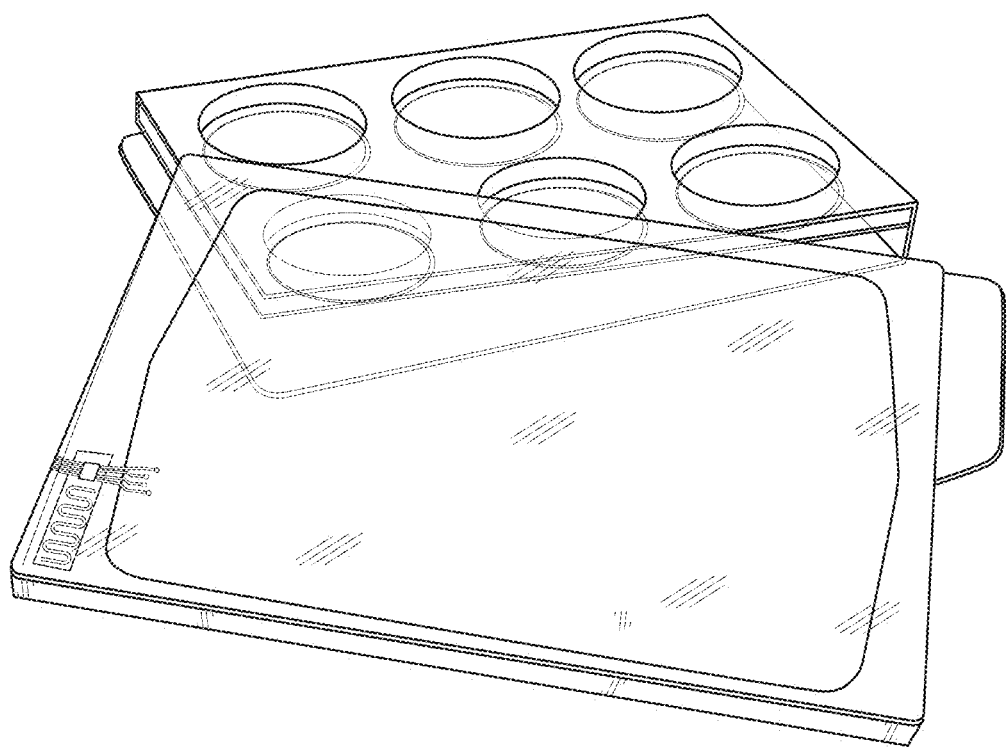
FIG. 1 presents a cassette for culturing adherent cells comprising a first and second film.

The invention relates to containers or cassettes for culturing adherent cells. The cassettes of the various embodiments offer numerous advantages over cell culture containers known in the art. For example, the cassettes and incubator permit automated detection of the cell culture environment, and automated passaging of cells, feeding of cells and sampling of cells. The cassettes also facilitate culture of large numbers of adherent cells in the presence of one or more compounds of interest. The cassettes allow for adherence of cells via methods that do not require chemical modification to detach the cells from the surface to which they adhere.

The incubators have an increased capacity for housing cells in culture and are a designed to allow for automated monitoring and maintenance of the culture environment including but not limited to maintenance of pH, $O_2$, $CO_2$, and cell density. The incubators provide for automated sampling and imaging of cells in culture. The cassettes and incubator provide significant increases in the efficiency of methods of culturing adhesion cells.

Definitions

Definitions. As used in this description and the accompanying claims, the following terms shall have the meanings indicated, unless the context otherwise requires:

As used herein, "cassette" means a sealed container for housing cells/and or tissues and culture media.

As used herein, a "film" comprises any material suitable for containing cells, including but not limited to polymer films, for example, polyester, polystyrene, Surlyn, polyolefins, cyclic olefin copolymers (COC), or poly(methylmetacrylate) (PMMA), membranes, for example, PVDF, cellulose, or Nylon semi-permeable membranes. In one embodiment the film is metallized to minimize gas transfer In certain embodiments, cells adhere to a tie layer present on the film. In other embodiments, a film is coated with at least one compound including but not limited to a nutrient, a growth factor, a hormone, a cytokine, an antibiotic, an adhesion molecule, a mineral, an antibody, a nucleic acid, including but not limited to nucleic acid probes, primers and oligonucleotides, ligands, enzymes such as polymerases, proteases, isomerases, cell components or cell markers, small molecules and dyes. In certain embodiments, the compound is living or dead cells (e.g., for use as a viral target, or a baseline control for determining cell concentration or baseline or basal levels of target protein expression). The cells can be stained or treated to allow for detection. In certain embodiments, the "film" is coated with a test compound to be screened for a particular activity of interest. The film can be of any dimensions such that a surface for culturing the desired number of cells is provided. The thickness of the film can be such that diffusion of material across the surface of the film can occur. In one embodiment, the thickness of the film is from 1 μM to 1 mM, for example, 10 μM to 500 μM, or 20 μM to 100 μM.

In one embodiment, the film comprises a tie layer(s) comprising a material that can be separated from or peeled off of the film.

Cells adhere to the tie layer and therefore are removed from the film when the tie layer reverts to monomers or small polymers that dissolve upon exposure to a particular treatment, and wherein cells are subsequently released. For example, in one embodiment, a tie layer comprises a photodepolymerizing material, or a material that, for example material that is thermoreversible, chemoreversible or enzymatically cleavable. Under the appropriate condition (light, heat, chemical environment) the tie layer reverts to monomers or small polymers that dissolve and release the cells. In one embodiment, film comprises a tie layer composed of a phase change material that allows the tie layer to be peeled off the film without reverting to monomers and small polymers that eventually dissolve, thereby providing a sheet of cells.

As used herein, a "frame" refers to a structure that is used in association with the film comprising a cassette. A "frame" can be either solid or flexible. In certain embodiments, a "frame" comprises at least one sensor as defined herein. A "frame" is located either between a first and second film or on the exterior of a certain layer of film, for example, around the perimeter of the film. In certain embodiments, the frame comprises polystyrene, PMMA, polyolefins such as polyethylene, surlyn, engineering thermoplastics and any thermoplastic, thermoset or composite thereof.

In certain embodiments, the film in combination with the frame is under tension.

The cassette can include frangible sealed regions or compartments containing, for example, a liquid or solid where a sustained squeeze just prior to use will burst the seal and swirl the components together. The multiple component pouches with internal frangible seals afford the opportunity to conveniently and inexpensively deliver portions with time-of-use mixing. This allows for extending the shelf life of cassettes dramatically. All of the biologically active components are maintained in a fluid chamber that the user or machine can burst in. In one embodiment, the frangible film is Surlyn, which does not contribute particulars to the mixtures when the seal is broken.

As used herein, a "sensor" detects or measures one or more properties of the cell and/or environment inside the cassette. A "sensor" can monitor, modify, record, indicate, or otherwise respond to one or more properties of the cell and/or the environment inside a cassette. According to the methods described herein, a sensor detects at least one of temperature, pH, $O_2$, $CO_2$ and cell density. In one embodiment, a sensor detects protein expression by detecting fluorescence, for example by a FISH assays. In other embodiments, the sensor is ligand-based or ligand-specific for detection of, for example, specific proteins or nucleic acids, apoptotic markers, nutrient levels, and/or the consumption rates of various media constituents.

A sensor can be located on the film and/or the frame comprising the cassette.

In certain embodiments, a "film" coated with a compound useful for altering a property of a cell or tissue and/or supporting cell growth and viability and/or facilitating adhesion of the cells to the film. A "compound" includes but is not limited to a nutrient, a growth factor, a hormone, a cytokine, an antibiotic, an adhesion molecule, a mineral, an antibody, a nucleic acid, including a nucleic acid probe, an antisense molecule, a primer and an oligonucleotide, a ligand for a receptor of interest, enzymes, for example, including but not limited to polymerases, proteases, isomerases etc. . . . a small molecule and a dye. The compound can be a cell(s), either living or dead, for use as a viral target, for defining a baseline level of cellular activity and/or protein or mRNA expression; and to establish a baseline for cell concentration. The cells can be living or dead, and stained or otherwise treated to facilitate detection. The "film" can also be coated with a test compound to be screened for a particular activity of interest or a therapeutic agent.

In certain embodiments, the cassette comprises a first and second layer of film, and further comprises one or more compartments. As used herein, a "compartment" refers to an enclosed section of the cassette, that can be used to house cells of interest such that they are separated from and are not in contact with cells that are present in the cassette but are located outside of the compartment. A "compartment" can include a sensor. The regions of the film comprising a compartment may be coated with at least one compound of interest. The compartment can comprise a particular cell media that is either different from or identical to media present in other compartments of the cassette. In certain embodiments, fluid is introduced to or removed from a "compartment" via a unique fluid line.

The invention also provides for cassettes wherein replicate samples of cells are adhered to the film at discrete locations but are not confined to a "compartment" as defined herein.

As used herein, "modulate" or "modulation" refers to increase or decrease.

As used herein, "decrease" as it refers to the level of activity of a cell or the level of expression of a marker, for example a protein, mRNA or antibody of interest by a cell, means that activity or expression is 1, 2, 3, 4, 5, 10, 15, 20, 25, 30, 35, 40, 45, 50, 100, 500, 1000 or 10,000-fold less before or after administration to or incubation in the presence of a cell with a compound of interest.

As used herein, "decrease" as it refers to the level of activity of a cell or the level of expression of a marker, for example a protein, mRNA or antibody of interest by a cell, means that activity or expression is 1, 5, 10, 15, 20, 25, 30, 35, 40, 45, 50, 55, 60, 65, 70, 75, 80, 85, 90, 95, 99 or 100% before or after administration to or incubation in the presence of a cell with a compound of interest.

As used herein "increased" as it refers to the level of activity of a cell or the level of expression of a marker, for example a protein, mRNA or antibody of interest by a cell, means that activity or expression is 1, 2, 3, 4, 5, 10, 15, 20, 25, 30, 35, 40, 45, 50, 100, 500, 1000 or 10,000-fold or more before or after administration to or incubation in the presence of a cell with a compound of interest.

As used herein "increased" as it refers to the level of activity of a cell or the level of expression of a marker, for example a protein, mRNA or antibody of interest by a cell is 1, 5, 10, 15, 20, 25, 30, 35, 40, 45, 50, 55, 60, 65, 70, 75, 80, 85, 90, 95, 99 or 100% greater before or after administration to or incubation in the presence of a cell with a compound of interest.

As used herein, the term "disease" includes any one or more of the following autoimmune diseases or disorders: diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves ophthalmopathy, sarcoidosis, primary biliary cirrhosis, uveitis posterior, and interstitial lung fibrosis.

In another embodiment, disease refers to any one of Wilson's disease, spinocerebellar ataxia, prion disease, Parkinson's disease, Huntington's disease, amytrophic lateral sclerosis, amyloidosis, Alzheimer's disease, Alexander's disease, alcoholic liver disease, cystic fibrosis, Pick's Disease, spinal muscular dystrophy or Lewy body dementia.

"Disease" also includes any one of rheumatoid spondylitis; post ischemic perfusion injury; inflammatory bowel disease; chronic inflammatory pulmonary disease, eczema, asthma, ischemia/reperfusion injury, acute respiratory distress syndrome, infectious arthritis, progressive chronic arthritis, deforming arthritis, traumatic arthritis, gouty arthritis, Reiter's syndrome, acute synovitis and spondylitis, glomerulonephritis, hemolytic anemia, aplastic anemia, neutropenia, host versus graft disease, allograft rejection, chronic thyroiditis, Graves' disease, primary binary cirrhosis, contact dermatitis, skin sunburns, chronic renal insufficiency, Guillain-Barre syndrome, uveitis, otitis media, periodontal disease, pulmonary interstitial fibrosis, bronchitis, rhinitis, sinusitis, pneumoconiosis, pulmonary insufficiency syndrome, pulmonary emphysema, pulmonary fibrosis, silicosis, or chronic inflammatory pulmonary disease.

"Disease" also refers to any one of cancer, tumor growth, cancer of the colon, breast, bone, brain and others (e.g., osteosarcoma, neuroblastoma, colon adenocarcinoma), chronic myelogenous leukemia (CML), acute myeloid leukemia (AML), acute promyelocytic leukemia (APL), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

As used herein, "diagnosing" or "identifying a patient or subject having" or "a patient or subject in need of treatment" refers to a process of determining if an individual is afflicted with a disease or ailment.

A subject is said to be treated for a disease, if following administration of an agent, one or more symptoms of the disease are decreased or eliminated.

"Treatment", or "treating" as used herein, is defined as the application or administration of a compound identified as treating a disease of interest, to a subject or patient, or application or administration of a compound identified as treating a disease of interest to an isolated tissue or cell line from a subject or patient, who has a disease or disorder, with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective amount" or "effective dosage" or "therapeutic dosage" is defined as an amount sufficient to achieve or at least partially achieve the desired effect. The terms "therapeutically effective dose" and "therapeutically effective amount" are defined as an amount sufficient to cure or at least partially arrest the disease and its complications in a patient already suffering from the disease.

As used herein, "treating" a disease refers to preventing the onset of disease and/or reducing, delaying, or eliminating disease symptoms, such as an increase in the extracellular level of a group of cytokines. By "treating" is meant restoring the patient or subject to the basal state as defined herein, and/or to prevent a disease in a subject at risk thereof. Alternatively, "treating" means arresting or otherwise ameliorating symptoms of a disease.

As used herein, "patient" or "subject" refers to a mammal that is diagnosed with a disease associated with an increase in the extracellular level of a group of cytokines.

The term "patient" or "subject" includes human and other mammalian subjects that receive either prophylactic or therapeutic treatment.

As used herein, "control subject" means a subject that has not been diagnosed with a disease and/or does not exhibit any detectable symptoms associated with the disease.

As used herein, "mammal" refers to any mammal including but not limited to human, mouse, rat, sheep, monkey, goat, rabbit, hamster, horse, cow or pig.

A "non-human mammal", as used herein, refers to any mammal that is not a human.

As used herein, "basal state" refers to the extracellular level of a group of cytokines of an individual who is not susceptible to a disease and who has no symptoms of a disease.

As used herein "monitoring the treatment" means determining whether, following treatment of a subject, for example, a subject diagnosed with a disease associated with an increased extracellular level of a group of cytokines, the subject has been treated such that the symptoms of the disease are arrested or otherwise ameliorated and/or the disease and/or its attendant symptoms are alleviated or abated.

As used herein, "pharmaceutically acceptable carrier" refers to a carrier for the administration of a therapeutic agent. Exemplary carriers include saline, buffered saline, dextrose, water, glycerol, ethanol, and combinations thereof.

As used herein, the term "small molecule" refers to a non-peptidic, non-oligomeric organic compound either synthesized in the laboratory or found in nature. Small molecules, as used herein, can refer to compounds that are "natural product-like". However, the term "small molecule" is not limited to "natural product-like" compounds. Rather, a small molecule is typically characterized in that it contains several carbon-carbon bonds, and has a molecular weight of less than 1500, although this characterization is not intended to be limiting for the purposes of the present invention. Examples of "small molecules" that occur in nature include, but are not limited to, taxol, dynemicin, and rapamycin. In certain other preferred embodiments, natural-product-like small molecules are utilized.

The cassettes and incubator can be used to culture adherent cells under conditions that are precisely regulated. The cells can be maintained in culture by automated methods. The cassettes and incubator are useful for performing methods of treating a disease, methods of diagnosing a disease, methods of monitoring disease treatment and methods of designing a treatment protocol. In addition, the cassettes and incubator facilitate screening for a compound, for example, a therapeutic.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION OF THE PREFERRED EMBODIMENTS

FIG. 1 presents one embodiment of a cassette comprising a first and second layer of film and a frame. The cassette can be prepared by a method including preparing a frame that is, for example, injected molded, comprises a laminate-layered core or cast core or center core, is 3D printed, machined or lasercut. In one embodiment, the frame is surrounded on the top and bottom by film, membrane, multilayer coated film or a combination thereof. In another embodiment, the frame is surround on the top and bottom with a thick film that is die-stamped, laser cut, etc. . . . .

The film is coated at least by any of the following methods: roll to roll coating, printing of certain regions of the film, for example PRP islets to which discrete populations of cells will adhere, reagents used for detection, spots, lanes or other structures, hydrophobic and hydrophilic regions to channel liquid flow within the cassette.

In other embodiments, the file is coated with a metallic substance or other vapor or gas control coatings, for example by chemical vapor deposit (CVD) or sputtering, gravure coating, skiving and any other method of applying a coating reagent, ink or dye to a film or surface known in the art.

In one embodiment, cells are introduced into a cassette using a sterilizable and/or disposable, microfluidic manifold located in the rear of the chamber that controls the flow of median to each of the cassettes. For automated introduction, a micro plate is inserted into the machine, and the cells are individually aspirated from the plate via a disposable or reusable sterilizable capillary device that interfaces with the manifold. The capillary is robotically moved or and through gates and microfluidics the flow can be directed. For example, a robot that traverses the entire back of the system, has a capillary injection port that butts against the array or the cassettes themselves and injects the cells. Movement of media in an out the cassette can occur via this process.

For manual injection the user can lift a corner of the film and inject via pipet (such a liftable corner is depicted in FIG. 1) then reseal (for example, via an adhesive); or the user can inject through a re-sealable port that is built into the film or frame or both of the cassette.

Figure 2:
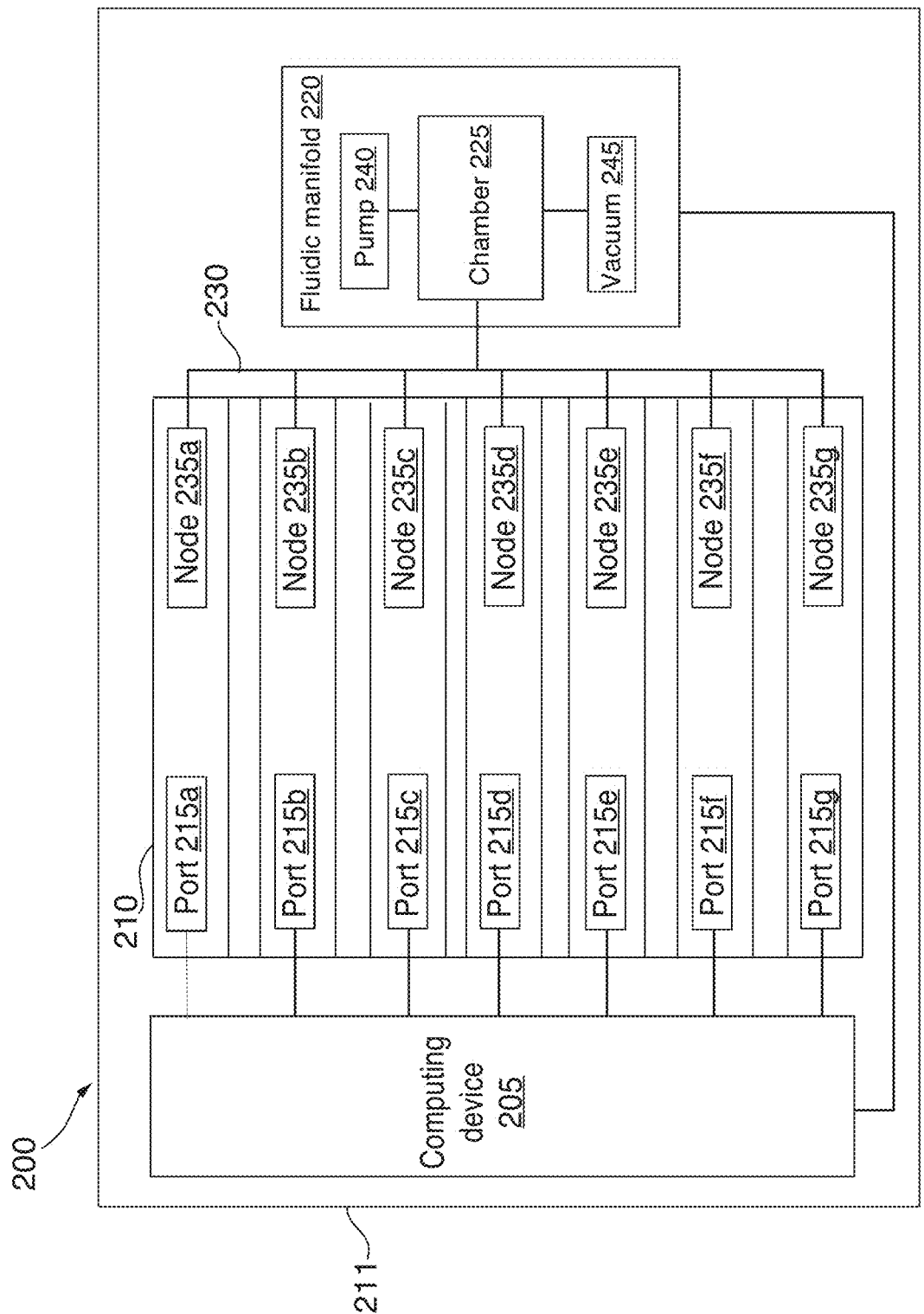
FIG. 2 presents a schematic diagram of an exemplary incubator that monitors and processes cell cultures disposed in cassettes.

FIG. 2 represents a schematic diagram of an exemplary incubator 200 that monitors and processes cell cultures disposed in cassettes. The incubator 200 includes a programmable computing device 205 that controls the incubator's operations. The computing device 205 includes a user interface, a processor, and a memory. The memory stores instructions for operating the incubator 200. The computing device 205 receives parameters from a user for processing cell cultures. The computing device 205 executes instructions according to the parameters to control components of the incubator 200. In various embodiments, the computing device 205 is configured to communicate over computer networks 305 with remote servers 310. The remote servers 310 may store data from the computing device 205 or communicate with users according to instructions from the computing device 205, as described in more detail below.

The incubator includes a chassis 210 disposed in a housing 211. The chassis 210 includes shelves that receive and support cassettes containing cell cultures. The shelves have a plurality of ports 215a, 215b, . . . ("215"). Each shelf has a port 215 that is coupled to the computing device 205. The shelf's port 215 interfaces with a connector on the cassette that is coupled to the cassette's circuitry, which receives data from sensors disposed within the cassette. The port 215 includes one or more connections for supplying power to the cassette's circuitry and/or receiving data collected by the circuitry's sensors. Data received through this port 215 is transmitted to the computing device 205.

The incubator 200 includes a fluidic manifold 220. A fluidic manifold 220 has a chamber 225 that houses a media of interest useful for cell culture. In some embodiments, the chamber 225 receives cell cultures extracted from cassettes. Further, although the figure depicts a single chamber 225, various embodiments of the incubator 200 may include multiple chambers for housing different media, or multiple chambers for receiving cell cultures from different cassettes. In this embodiment, a conduit 230 extends from the chamber 225 to shelves in the chassis 210. The conduit 230 includes nodes 235a, 235b, . . . ("235") that can be coupled to corresponding nodes on cassettes. Although the figure depicts a single conduit that connects to each of the cassettes, alternative embodiments may include multiple conduits, each of which is coupled to a distinct cassette or a subset of the cassettes.

In certain embodiments, a pump 240 coupled to the fluidic manifold 220 can propel media in the chamber 225 through a conduit into one or more of the cassettes. In further embodiments, a vacuum 245 coupled to the fluidic manifold 220 extracts the contents of one or more cassettes into a chamber. In some embodiments, the fluidic manifold 220 extracts the contents of a cassette into the same chamber used for propelling media into cassettes in the incubator. In other embodiments, the fluidic manifold 220 includes separate chambers for housing media to propel into cassettes and receiving contents extracted from cassettes.

In some embodiments, the incubator 200 has one or more image capturing devices and robotic arms for positioning the devices within the housing 211. The computing device 205 operates the robotic arms to position an image capturing device over a cell culture in a cassette. The computing device 205 operates the image capturing device to obtain an image of a cell culture.

Figure 3:
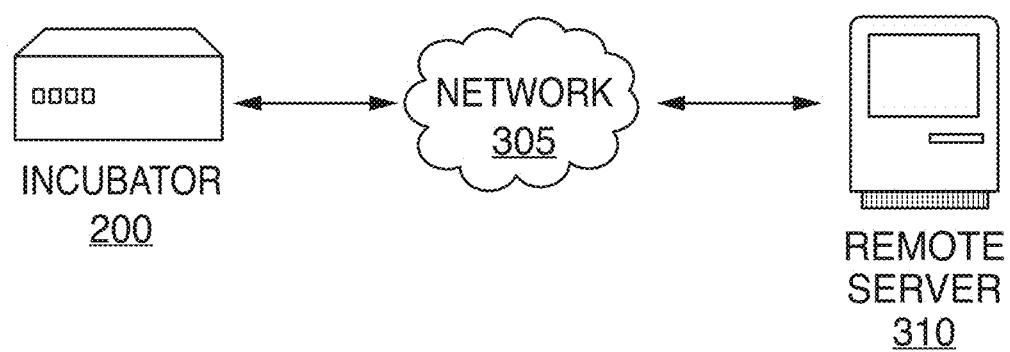
FIG. 3 depicts an exemplary incubator connected over a computer network to one or more remote servers.
Figure 4:
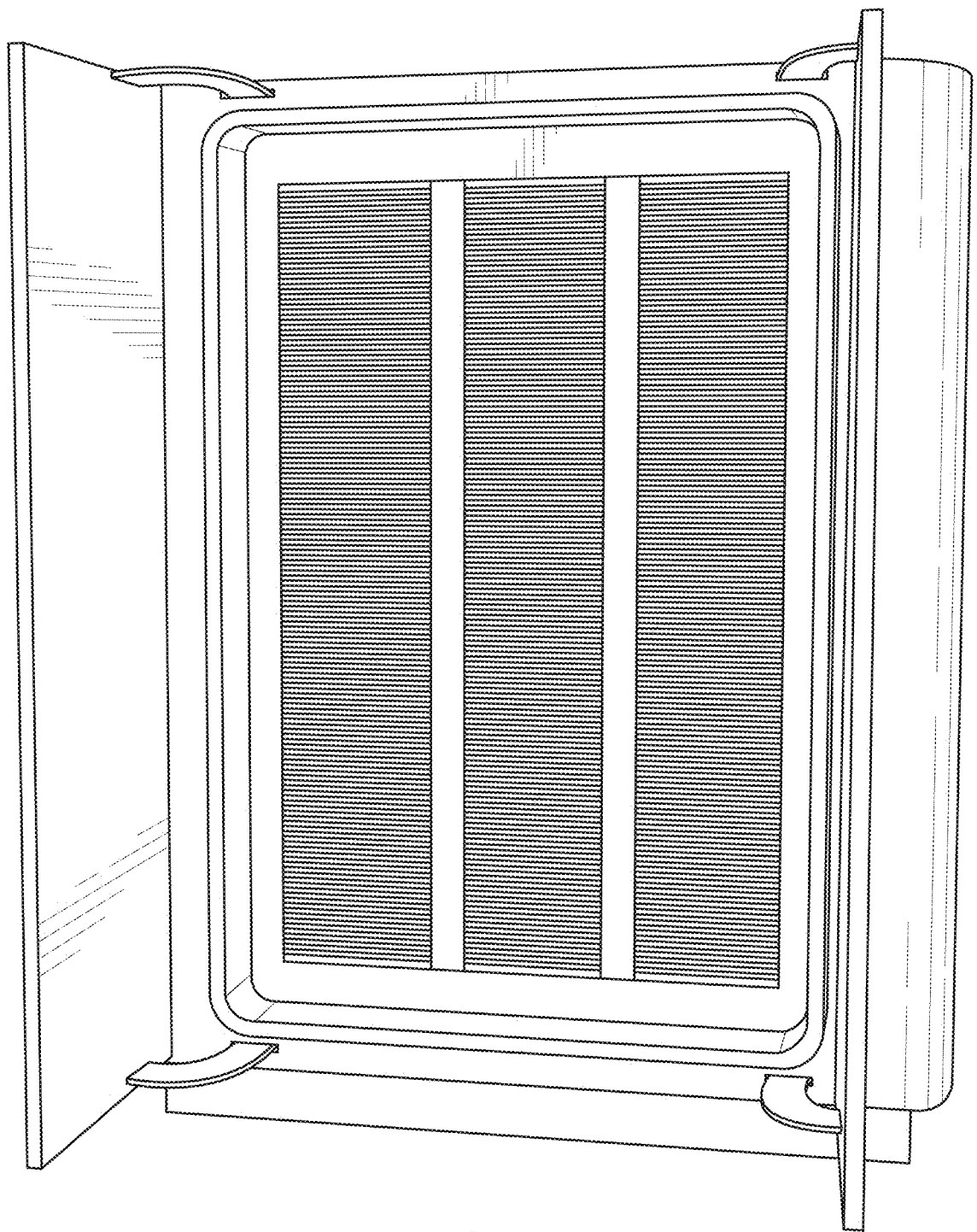
FIG. 4 presents the interior of an exemplary incubatory.
Figure 5:
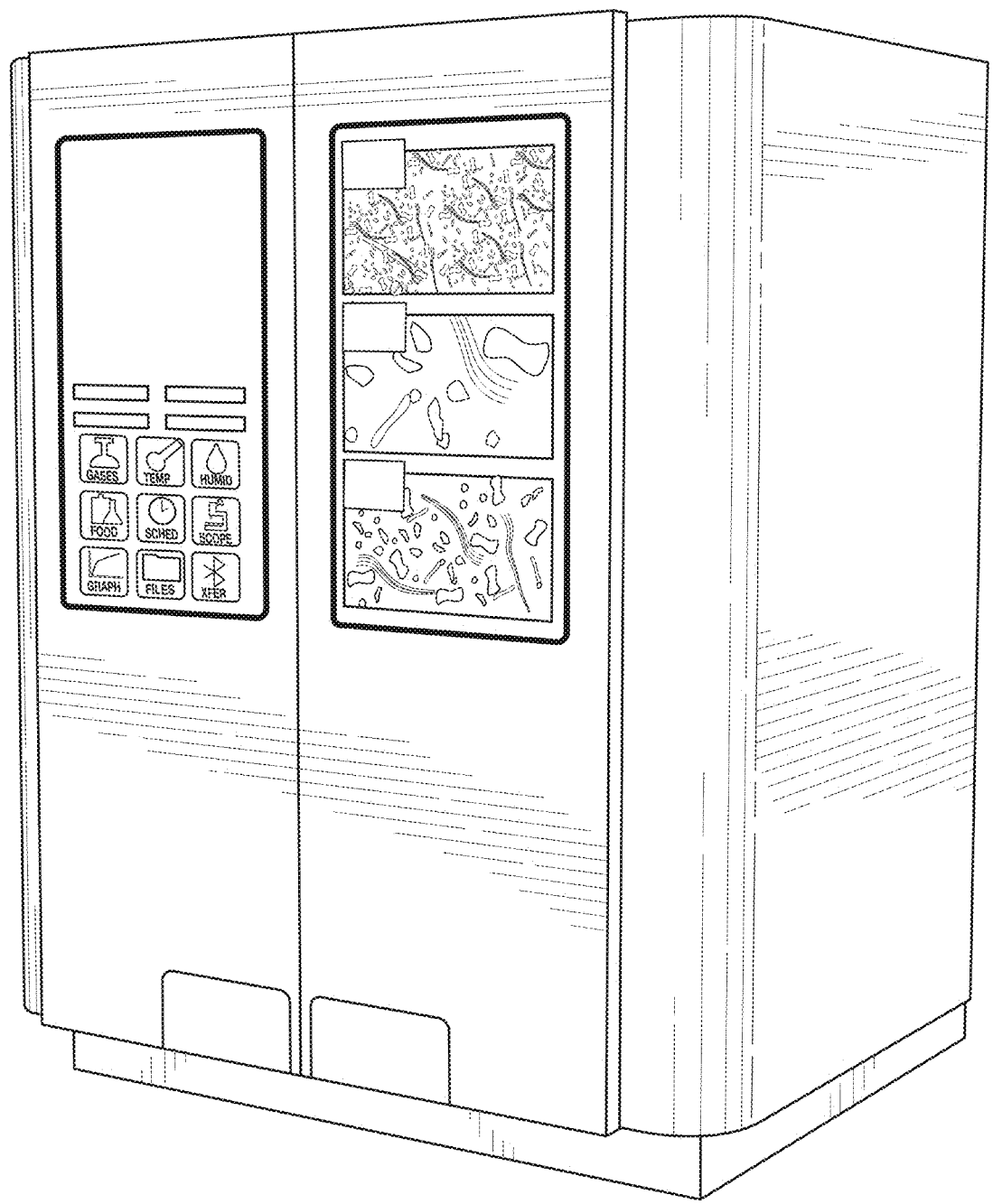
FIG. 5 presents an exemplary incubator.
Figure 6:
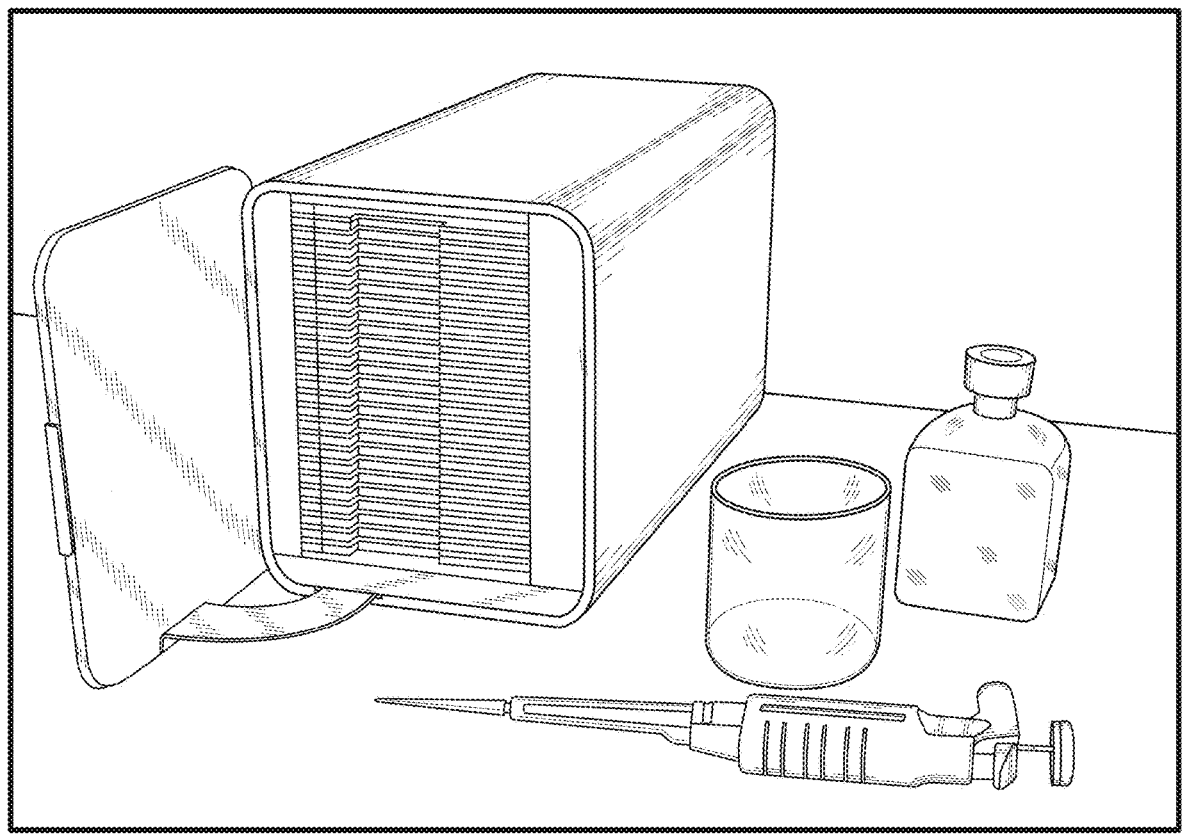
FIG. 6 presents the interior of an exemplary table top model of an incubator.
Figure 7:
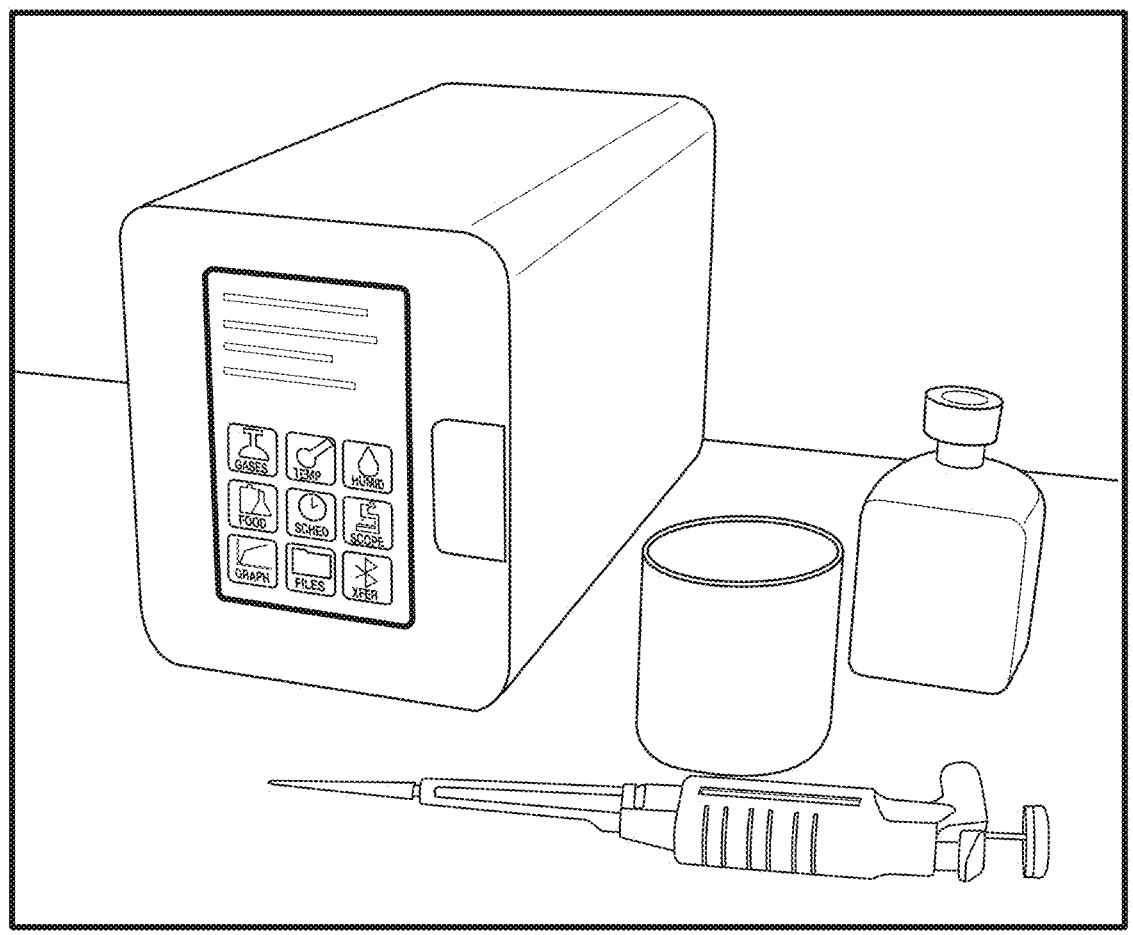
FIG. 7 prevents an exemplary table top model of an incubator.

FIG. 3 depicts the incubator 200 connected over a computer network 305 to one or more remote servers 310. The computing device 205 connects to the remote server(s) 310 via a local area connection (LAN), wide area connection (WAN), the Internet, or any computer network. In some embodiments, the computing device 205 transmits data regarding a cell culture, for example, pH and/or cell density, and environmental conditions within cassettes to a remote server 310 for storage. The server 315 stores the data. In some embodiments, the computing device 205 transmits messages to a remote server 315 for communicating with a user of the incubator. In turn, the remote server 315 sends the messages to a user.

In operation, a user introduces cells in combination with a media of interest into the cassettes and inserts the cassettes into the shelves of the incubator 200. When the user connects the connector on the cassette with the shelf's port 215, the computing device 205 detects the presence of the cassette. In some embodiments, the computing device 205 powers the cassette's circuitry by supplying a power signal through the port 215. The computing device 205 initializes a file for storing data on the environmental conditions of the cassette. The computing device 205 receives data collected by sensors in the cassette, such as temperature, cell density, and pH. In some embodiments, the computing device 205 stores the data in the file associated with the cassette. In other embodiments, the computing device 205 discards the data until the device 205 receives processing instructions from the user.

A user programs the computing device 205 to process cell cultures disposed in cassettes in the incubator 200. In some embodiments, the user programs the computing device 205 from a user interface disposed on the incubator 200. The user interface displays a menu of parameters for the user to select. For example, the user can select the temperature and humidity at which the incubator will maintain the environment in the cassettes. The user can select the media to introduce into the cassettes during processing. In certain embodiments, the user interface displays the % concentration of a gas, for example, O2 or CO2, the temperature inside the incubator, the composition and/or volume and/or pH of the media, or the amount of other substances present in the incubator's chambers, and the user can supply the incubator with additional resources, if necessary.

The user can create a schedule of actions with respect to the cell cultures. Some of the actions may be directed to monitoring the cell cultures. For example, the user may configure the incubator to begin beeping every 6 hours, thereby alerting the user to check conditions of the cell cultures. In another example, the user may configure the incubator to send the user a short message service (SMS) communication every 6 hours, for the same purpose. The user may input a mobile telephone number at which the user is capable of receiving SMS communication. Every six hours, the computing device 205 sends an instruction to the remote server 310 to send a reminder message to the user's mobile telephone number. In response, the remote server 310 creates the corresponding SMS communication and sends the same to the telephone number.

In a similar example, the user may configure the incubator to capture an image of the cells present in a particular cassette and e-mail the image to the user every 6 hours. The user may input an e-mail address. Every six hours, the computing device 205 operates a robotic arm to position an image capturing device over the cassette of interest, capture an image, and send the image and e-mail address to a remote server 310. The remote server 310 creates an e-mail message with the image and sends the same to the user.

Some of the actions may be directed to maintaining environmental conditions within the cassette. For example, the user can select a desired pH level for a cell culture, an acceptable level of deviation from the desired pH level, and media for adjusting the pH level in a cassette. Thus, if the pH level in a cassette becomes too basic, the fluidic manifold 220 flows additional media of the user's choosing into the cassette. Likewise, the fluidic manifold 220 flows a different media selected by the user if the pH level becomes too acidic. In another example, the user can select a desired level of feed for the cell culture. For example, the user can select a desired concentration, or a minimum concentration, of feed present in the cell culture's environment. When the concentration of feed drops below the desired or minimum level, the fluidic manifold 220 flows additional feed into the cassette.

Some of the actions may be directed to processing a cell culture within a cassette. An action may depend upon elapses of time, conditions regarding the cell culture itself or the environment in the cassette (e.g., pH, temperature, cell density), or user initiative. In various examples, the user may schedule the incubator to flow a media into ten cassettes comprising cell cultures, heat the cassettes until they reach a desired temperature, and maintain the desired temperature for a particular length of time. The user may schedule the incubator to monitor the pH levels of the cassettes and flow a selected media through the cassettes once the pH levels reach a user selected threshold. The user may schedule the incubator to monitor the cell density of cultures and passage the same once the cell density reaches a desired threshold. The fluidic manifold 220 flows the passaging media into the cassettes, and the vacuum extracts the cells into a chamber for retrieval by the user.

In some embodiments, the user may schedule the incubator to send alerts whenever a programmed condition is met. For example, a user may schedule the incubator to flow a media into cassettes when the pH level in the cassette drops below a threshold level. The computing device 205 continues to receive data about the pH levels from the cassettes, and when the pH levels drop to the threshold, the computing device 205 sends the user an alert (e.g., an e-mail message, an SMS message). Thus, the user may be informed of an experiment's progress.

In some embodiments, the user may schedule the incubator to monitor the cell density and send the user an image of a culture when the detected cell density reaches a desired threshold. The incubator may require user approval to passage the cells, or to enact another process. If the incubator does not receive such approval, the incubator may maintain the environmental conditions of the cassette and continue sending images to the user, according to a predetermined schedule. Once the user approves an image of the cell cultures, based on its density, the incubator may passage the cell culture, or perform some other desired process.

Processing actions may include any manipulation of the cell cultures, according to any conditions. The user can schedule a series of processes, based on any of the parameters described herein. For example, the user can instruct the incubator to flow medium A into the cassettes and allow the cells to incubate for a particular period of time. After the four hours have elapsed, the incubator may flow medium B into the cassettes until the pH level for each cassette has dropped to a user selected level. Then, the incubator may raise the temperature of the incubator to a desired temperature. Once the temperature reaches the desired temperature, the fluidic manifold may flow medium C into the cassettes to feed the cell cultures. The incubator may monitor the cell density of each cassette. When the cell density of a cassette reaches a user selected threshold, the fluidic manifold may flow a passaging reagent into the cassettes, the cells are incubated for a predetermined period of time in the presence of the reagent such that the cells dissociate from the film comprising the cassette, and vacuum the cassettes' contents into a chamber from which the cells can be isolated. Processes according to similar parameters, or sequences thereof, may also be deployed.

In some embodiments, the user can program the computing device 205 remotely. The user can log into a remote computing device 205 that executes an application that instructs the sequence of events required to perform a particular experimental analysis. The application may include a similar user interface to the one depicted on the incubator. The user may create a schedule of actions for the incubator, as described herein. The computing device 205 executing the application transmits the user controls over a computer network 305 to the incubator, and the incubator's computing device 205 stores the controls in its memory.

Once the user inputs the schedule of actions, the computing device 205 receives data about environmental conditions in the cassettes through the ports 215 and store the data in files corresponding to the cassettes. In some embodiments, the computing device 205 stores the data in its local memory. The user can access the data through the user interface. From the menu, the user can select the file corresponding to a cassette of interest, and the computing device 205 displays the cassette's data. The user can scroll through the data to view data at different intervals of time.

In other embodiments, the computing device 205 transmits the data over a computer network 305 to a remote server for storage. Users can access the data on the remote servers 310. In some embodiments, using an application executing on a computing device, a user can log into an account on the remote server 310. The user may view the data collected by the incubator 200 and transmitted to the remote server 310. In this manner, the user may monitor the progress of the cell cultures and the environmental conditions through which the cell cultures have progressed.

Various embodiments may be implemented at least in part in any conventional computer programming language. For example, some embodiments may be implemented in a procedural programming language (e.g., "C"), or in an object oriented programming language (e.g., "C++"). Other embodiments may be implemented as preprogrammed hardware elements (e.g., application specific integrated circuits, FPGAs, and digital signal processors), or other related components.

In an alternative embodiment, the disclosed apparatus and methods may be implemented as a computer program product for use with a computer system. Such implementation may include a series of computer instructions fixed either on a tangible medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a tangible removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments may be implemented as a combination of both software (e.g., a computer program product) and hardware. Still other embodiments are implemented as entirely hardware, or entirely software.

EXAMPLES

Example 1—Methods of Culturing Cells

A cell of interest is introduced into a cassette of the invention via a sterilizable and/or disposable microfluidic manifold located in the rear of the chamber that controls the follow of medium to a cassette of the invention. A cell is introduced either manually or via automated methods. A cell is introduced in combination with a media of interest into a cassette and the cassette is inserted into an incubator according to the invention. In certain embodiments, the cell is cultured in the presence of at least one agent known to have a desired effect on the cell, for example, increase or decrease an activity of the cell, or increase or decrease expression of a marker of the cell. The cell can also be cultured in the presence of an agent identified as treating a disease. Cells are cultured at a density know to be appropriate for optimal growth of that particular cell type.

Example 2—Treatment of a Disease

Cells are removed from a subject in need of treatment. Cells that are removed can be present in a biological sample including but not limited to, blood, saliva, urine and tissue. The cells are transferred into the cassette of the invention and cultured in the presence of at least one agent identified as treating the disease. Following the culture period, the cells are reintroduced into the subject, for example, by injection, thereby treating the disease.

Various embodiments of the present invention may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

The embodiments described above are intended to be merely exemplary; numerous variations and modifications will be apparent to those skilled in the art. All such variations and modifications are intended to be within the scope of the present invention as defined in any appended claims.

What is claimed is:

1. A cassette for culturing adherent cells comprising a sealable container for culturing adherent cells therein having a frame and a first film and a second film, wherein the cells are received between the first and second films and at least one sensor on at least one of the first film or the second film for sensing cell density of the cells between the first film and the second film.

2. The cassette of claim 1, wherein at least one of the first film or the second film is coated with at least one compound selected from the group consisting of: a nutrient, a growth hormone, a cytokine, an antibiotic, an adhesion molecule, a mineral, an antibody, a nucleic acid probe, a primer, an oligonucleotide, an antisense oligonucleotide, a ligand, an enzyme, cell components, cell markers, cells, a dye, and a test compound.

3. The container of claim 1, wherein the at least one sensor additionally detects at least one of temperature, pH, $O_2$, $CO_2$, protein, nucleic acid, apoptotic markers, nutrient levels and the rate of consumption of a media component.

4. The cassette of claim 1, wherein at least one of the first film or the second film comprises an adherent layer to which cells can adhere.

5. The cassette of claim 4, wherein cells adhere to discrete locations on the adherent layer.

6. The cassette of claim 4, wherein the cells can be removed from the layer to which they adhere by a method selected from the group consisting of: increasing or decreasing the pH, increasing or decreasing light exposure, and enzymatic degradation.

7. The cassette of claim 1, wherein the at least one sensor is present on the frame.

8. The cassette of claim 1, further comprising an inlet for introducing fluids and an outlet for removing fluids.

9. The cassette of claim 1, wherein at least one of the first film or the second film comprises a material selected from the group consisting of: polymer films, polyester, polystyrene, surlyn, polyolefins, cyclic olefin polymers, poly(methyl metacrylate), polyvinylidene difluoride (PVDF) membranes, cellulose membranes, and nylon semi-permeable membranes.

10. The cassette of claim 1, wherein a tissue sample is cultured.

11. The cassette of claim 1, wherein the sealable container comprises more than one compartment.

12. The cassette of claim 11, wherein each compartment comprises a sensor.

13. The cassette of claim 12, wherein the sensor of each compartment has a different sensing function.

14. The cassette of claim 11, wherein at least one of the first film or the second film in each compartment is coated with at least one compound selected from the group consisting of: a nutrient, a growth hormone, a cytokine, an antibiotic, an adhesion molecule, a mineral, an antibody, a nucleic acid probe, a primer, an oligonucleotide, an antisense oligonucleotide, a ligand, an enzyme, cell components, cell markers, cells, a dye, and a test compound.

15. A method of culturing cells comprising incubating cells in the cassette of claim 1.

16. The method of claim 15, further comprising an automated step of feeding the cells.

17. The method of claim 15, further comprising an automated step of passaging the cells.

18. The method of claim 15, wherein at least one film of the cassette is coated with a compound of interest.

19. The method of claim 15, wherein the cassette is housed in an incubator.

* * * * *